United States Patent [19]
Truex et al.

[11] Patent Number: 5,683,435
[45] Date of Patent: Nov. 4, 1997

[54] IMPLANTABLE MEDICAL DEVICE HAVING SHIELDED AND FILTERED FEEDTHROUGH ASSEMBLY AND METHODS FOR MAKING SUCH ASSEMBLY

[75] Inventors: Buehl E. Truex, Glendora; Scott R. Gibson, Granada Hills; Alvin H. Weinberg, Moorpark, all of Calif.

[73] Assignee: Pacesetter, Inc., Sylmar, Calif.

[21] Appl. No.: 748,307

[22] Filed: Nov. 13, 1996

Related U.S. Application Data

[62] Division of Ser. No. 565,204, Nov. 13, 1995, Pat. No. 5,620,476.

[51] Int. Cl.$^6$ .................................................. A61N 1/375
[52] U.S. Cl. ................................... 607/37; 174/50.52
[58] Field of Search .............................. 607/2, 36–38; 174/17.08, 50.5, 50.52; 29/830, 840, 846

[56] References Cited

U.S. PATENT DOCUMENTS

| | | | |
|---|---|---|---|
| 4,420,652 | 12/1983 | Ikeno | 174/52 |
| 5,144,946 | 9/1992 | Weinberg et al. | 607/2 |

*Primary Examiner*—William E. Kamm
*Assistant Examiner*—George R. Evanisko

[57] ABSTRACT

A wireless feedthrough assembly, for coupling leads received in the receptacles of a connector assembly to the electronic circuit within a cardiac pacemaker, includes a weld ring mounted in hermetically sealed fashion within a housing wall of the pacemaker and itself hermetically sealed to an intermediate portion of an elongated, multilayered structure. The multilayered structure includes layers of electrically insulating ceramic material on opposite sides of a planar array of printed conductors extending between a first portion of the structure within the connector assembly and an opposite second portion of the structure within the pacemaker. Connector pads at the ends of the printed conductors within the first portion are coupled to the receptacles of the connector assembly, while contact pads at the exterior of the second portion and coupled by vias to connector pads at the ends of the printed conductors are coupled to the electronic circuits within the pacemaker. Printed ground planes on the multilayered structure form a conductive envelope which shields the printed conductors from electric fields. The contact pads include positive and ground contacts to which are coupled discrete filtering capacitors for limiting the spectrum of frequencies receivable by the connector assembly. A method for making the aforedescribed feedthrough assembly.

3 Claims, 3 Drawing Sheets

IMPLANTABLE MEDICAL DEVICE HAVING SHIELDED AND FILTERED FEEDTHROUGH ASSEMBLY AND METHODS FOR MAKING SUCH ASSEMBLY

This application is a divisional of application Ser. No. 08/565,204 filed on Nov. 13, 1995 now U.S. Pat. No. 5,620,476.

FIELD OF THE INVENTION

The present invention relates generally to implantable medical devices, such as cardiac pacemakers, cardioverters and defibrillators, and more particularly, to a wireless feedthrough assembly for connecting electronic circuits within an implantable medical device to the connector top and for providing electric field shielding and filtering.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart via an external connector assembly having lead-receiving receptacles. The appended claims are not intended to be limited, however, to any specific example or embodiment described herein.

Cardiac pacemakers, and other implantable medical devices such as cardiac defibrillators, are hermetically packaged to isolate the device from the body environment. Such devices require that electrical signals be passed between the packaged device and its external connectors, without compromising the hermeticity of the package. Depending on the configuration of the implantable device, there may be multiple electrical paths required between the device and its external connectors. These paths must be electrically and mechanically integrated with the device to provide a safe, long-term arrangement which does not compromise the hermetic package.

Typically, electrical coupling between the electronic circuits of the implantable device and the external connections provided by a connector assembly mounted outside of the implantable device are provided by a feedthrough assembly. The feedthrough assembly extends through the hermetically sealed outer wall of the device and into the connector assembly so as to couple the electronic circuits within the implantable device to lead-receiving receptacles within the connector assembly. Common feedthrough assemblies contain a number of wires equal to the number of electrical paths required for the configuration. The wires are placed in a ceramic sleeve and are sealed and mechanically secured to the sleeve, such as by brazing. The ceramic sleeve is secured to a weld ring, such as by brazing, following which the weld ring is integrated into the housing wall of the implantable device, such as by laser welding. The resulting feedthrough assembly has many individual seals and exposed lengths of wire.

Feedthrough assemblies of the type described have a number of potential problems. One such problem results from the large number of seals required. Because the plurality of wires and the weld ring each require a separate seal, the large number of seals increases the chances of a compromised seal and the resulting loss of hermeticity. Moreover, the exposed wires act as an antenna for environmental noise sources. Such noise compromises the quality of the signal transmitted, and this can lead to misinterpretation by the implantable device. Additionally, the wires can be damaged by misalignment or bending during handling of the feedthrough assembly.

It would therefore be desirable to provide a feedthrough assembly which eliminates the use of wires, reduces the number of seals required so as to reduce the potential for lost hermeticity, and eliminates the possibility of wire misalignment or bending during the handling.

It would furthermore be desirable to provide a feedthrough assembly which incorporates electric field shielding to protect the electrical paths from potential noise sources, and thus potentially inaccurate signals.

It would still furthermore be desirable to provide a feedthrough assembly which integrates signal filtering within the assembly itself, so as to focus the spectrum of frequencies to be interpreted by the implantable device.

SUMMARY OF THE INVENTION

Briefly stated, the present invention provides a feedthrough assembly in which plural wires are eliminated in favor of a single, monolithic structure of elongated configuration which extends through and is hermetically sealed to a sealing device such as a weld ring. The weld ring is, in turn, hermetically sealed within the housing wall of the implantable device. The monolithic structure comprises a multilayered structure in which an array of printed conductors provides the connections between the electronic circuits of the implantable device and the lead-receiving receptacles of the connector assembly. Electric field shielding of the printed conductors is provided by a conductive boot surrounding the printed conductors and being coupled to ground. The conductive boot may be provided by printed ground planes on opposite sides of the printed conductors within a multilayered structure. Filtering is provided by capacitors coupled between positive contacts and ground contacts within a second portion of the feedthrough assembly residing within the implantable device.

In accordance with a specific, exemplary embodiment of the present invention, the feedthrough assembly includes an elongated, multilayered structure having an intermediate portion thereof hermetically sealed to the inside of a weld ring between opposite first and second portions residing within the connector assembly and the interior of the implantable device, respectively. The multilayered structure includes a generally planar array of printed conductors extending between the opposite first and second portions, and comprised of positive traces surrounded by a ground trace. The positive traces terminate at connector pads within the first portion, which connector pads are coupled to the lead-receiving receptacles of the connector assembly. Opposite ends of the positive traces within the second portion terminate in connector pads which are coupled by vias to contact pads at the exterior of the second portion. Such contact pads are coupled to the electronic circuits of the implantable device.

The multilayered structure comprises a laminate of electrically insulating ceramic layers, with first and second ones of the ceramic layers being disposed on opposite sides of and insulating the printed conductors from opposite first and second printed ground planes. The first and second ground planes are coupled by vias extending through the first and second ceramic layers to the ground trace, to form a grounded conductive envelope surrounding the printed conductors. The grounded envelope shields the printed conductors from electric fields.

The laminate of ceramic layers includes third and fourth layers of ceramic disposed on opposite sides of the first and second ground planes from the first and second ceramic layers, respectively. The third ceramic layer mounts the contact pads at the exterior of the second portion. The contact pads include positive contacts coupled to the positive traces of the printed conductors by vias extending through apertures in the third ceramic layer, the first ground plane and the first ceramic layer. The contact pads also include ground contacts coupled to the first ground plane by vias extending through apertures in the third ceramic layer. The positive contacts are coupled to the electronic circuits of the implantable device. At the same time, discrete filtering capacitors coupled between the positive and ground contacts on the third ceramic layer provide filtering to limit the spectrum of frequencies receivable by the electronic circuits.

In a preferred method of making a feedthrough assembly in accordance with the present invention, a plurality of ceramic layers are first formed, following which apertures and vias are created in appropriate ones of the layers. Next, vias are filled and conductive traces, ground planes and contacts are printed on the appropriate ceramic layers. The ceramic layers are then stacked and laminated with printing in an appropriate configuration to form a ceramic assembly. The ceramic assembly is fired to form a monolithic hermetic structure. The structure is then shaped to a desired final configuration. Conductive material is applied to a selected surface portion of the structure, at the intermediate portion thereof, before placing a weld ring over the selected surface portion and brazing to form a hermetic seal between the structure and the weld ring. Filtering capacitors are then attached to the contacts at the exterior of the second portion, to complete the feedthrough assembly,

BRIEF DESCRIPTION OF THE DRAWINGS

Further objects, advantages and features of the invention will become apparent from the detailed description of the preferred embodiment when read in conjunction with the accompanying drawings, in which.

DESCRIPTION OF THE PREFERRED EMBODIMENT

Figure 1:
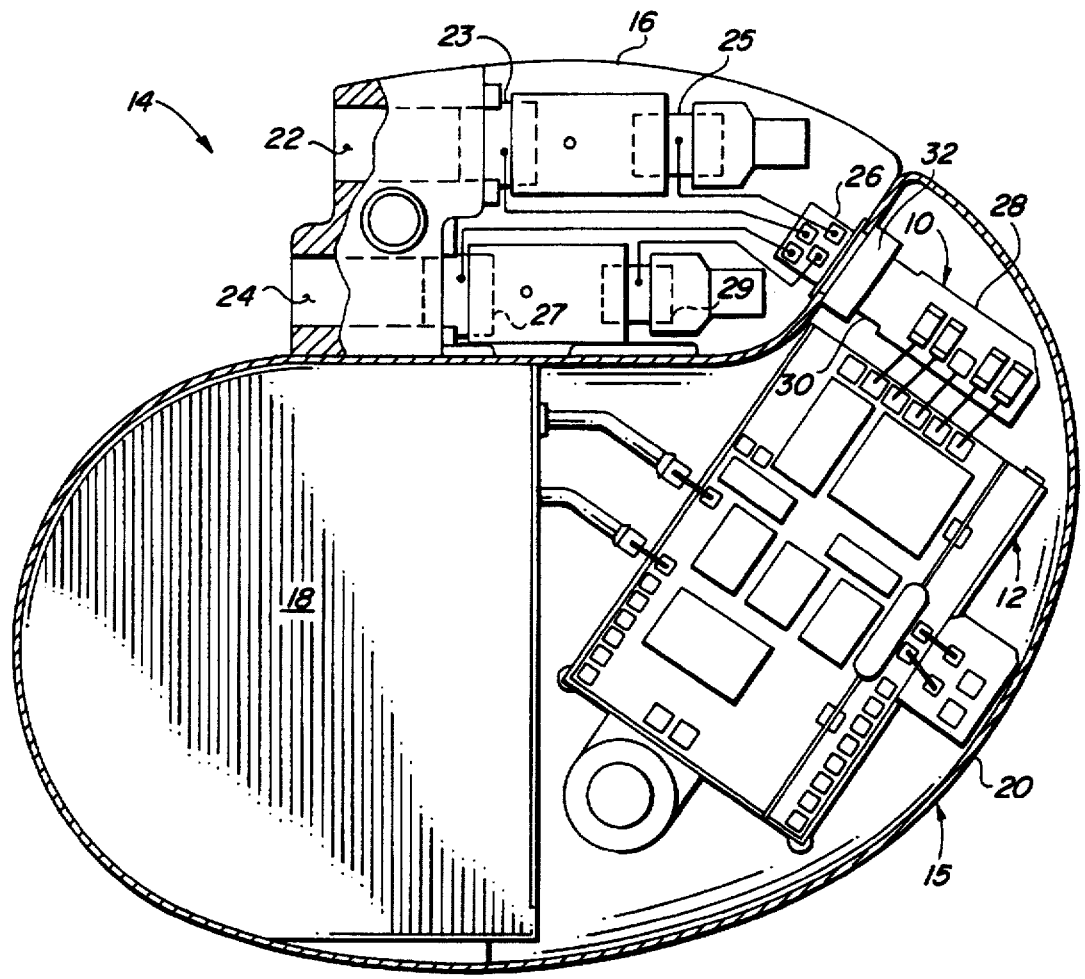
FIG. 1 is a sectional view of a cardiac pacemaker and an external connector assembly in which a feedthrough assembly according to the invention provides electrical coupling therebetween.

In FIG. 1, there is shown a feedthrough assembly 10 in accordance with the present invention for electrically coupling the electronic circuits 12 of an implantable medical device in the form of a cardiac pacemaker 14 to a connector assembly 16 mounted external to the hermetically sealed housing 15. The electronic circuits 12 are powered by a battery 18, and both the electronic circuits 12 and the battery 18 are contained within the hermetically sealed housing 15 having a housing wall 20. The connector assembly 16, which is mounted at the outside of the wall 20 of the pacemaker 14, includes a plurality of receptacles 22 and 24 for receiving transvenous pacing leads in conventional fashion. Connector blocks 25 and 29 are employed to make electrical connection to the pin terminals of an atrial and ventricular implantable leads (not shown), respectively. Connector blocks 23 and 27 are employed to make electrical connection to the ring terminals of the atrial and ventricular implantable leads (not shown), respectively.

The feedthrough assembly 10 has a first portion 26 thereof residing within the connector assembly 16 and electrically coupled to the connector block 23, 25, 27, 29 located within the receptacles 22 and 24.

Electrical connection between the feedthrough assembly 10 and the connector blocks 23, 25, 27 and 29 may be made with conventional wires or may include a plurality of conductor ribbons formed as a set in a predetermined number, shape and spacing, as taught by commonly assigned U.S. Pat. No. 5,282,841 (Syszkowski) in which the conductor ribbons would extend between respective ones of the connector blocks 23, 25, 27 and 29 and a respective connector pad at the first portion 26 of the feedthrough assembly 10. U.S. Pat. No. 5,282,841 is hereby incorporated by reference in its entirety.

An opposite second portion 28 of the feedthrough assembly 10 resides within the pacemaker 14 and is electrically coupled to the electronic circuits 12. As described in detail hereafter, the feedthrough assembly 10 has an intermediate portion 30 thereof between the first and second portions 26 and 28 disposed within and hermetically sealed to a weld ring 32. The weld ring 32 is mounted in the housing wall 20 of the pacemaker 14 in hermetically sealed fashion.

Figure 2:
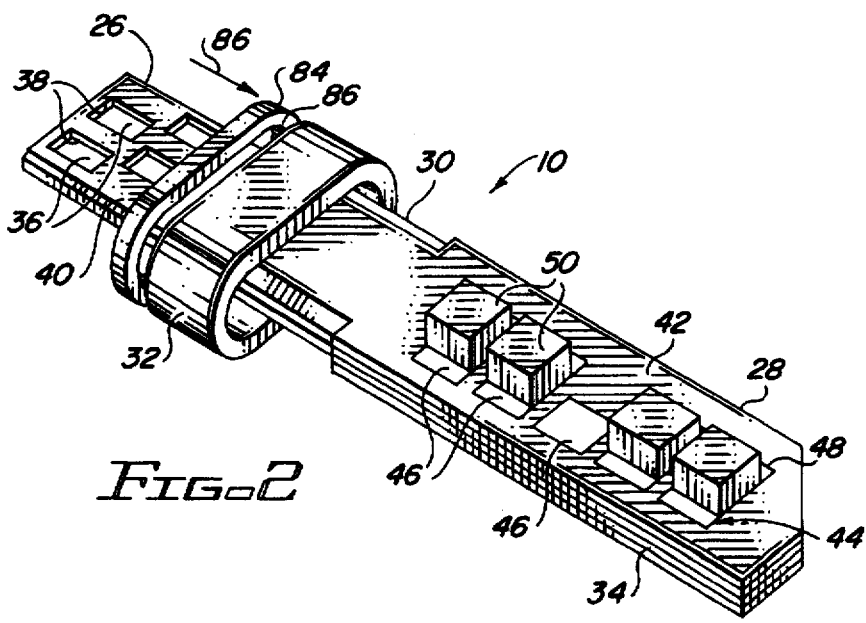
FIG. 2 is a perspective view of the feedthrough assembly of FIG. 1.

The feedthrough assembly 10 is shown in greater detail in FIG. 2. As shown therein, the feedthrough assembly 10 includes the weld ring 32 and an elongated, multilayered structure 34. The multilayered structure 34 extends through and is hermetically sealed to the interior of the weld ring 32 at the intermediate portion 30. The first and second portions 26 and 28 reside at opposite sides of the weld ring 32. As described in detail hereafter, the multilayered structure 34 includes a generally planar array of printed conductors extending along the length of the elongated multilayered structure 34 and being comprised of positive traces surrounded by a ground trace. The positive traces terminate in connector pads 36 at the first portion 26. Apertures 38 within an electrically insulated ceramic layer 40 of the multilayered structure 34 expose the connector pads 36 to facilitate connection thereof to the receptacles 22 and 24 of the connector assembly 16 shown in FIG. 1.

The second portion 28 of the feedthrough assembly 10 has a ceramic layer 42 extending along a top portion thereof and mounting a plurality of contact pads 44 thereon. The contact pads 44 include a plurality of positive contacts 46 and a plurality of ground contacts 48. A plurality of filtering capacitors 50 are coupled between the positive contacts 46 and the ground contacts 48.

Figure 3:
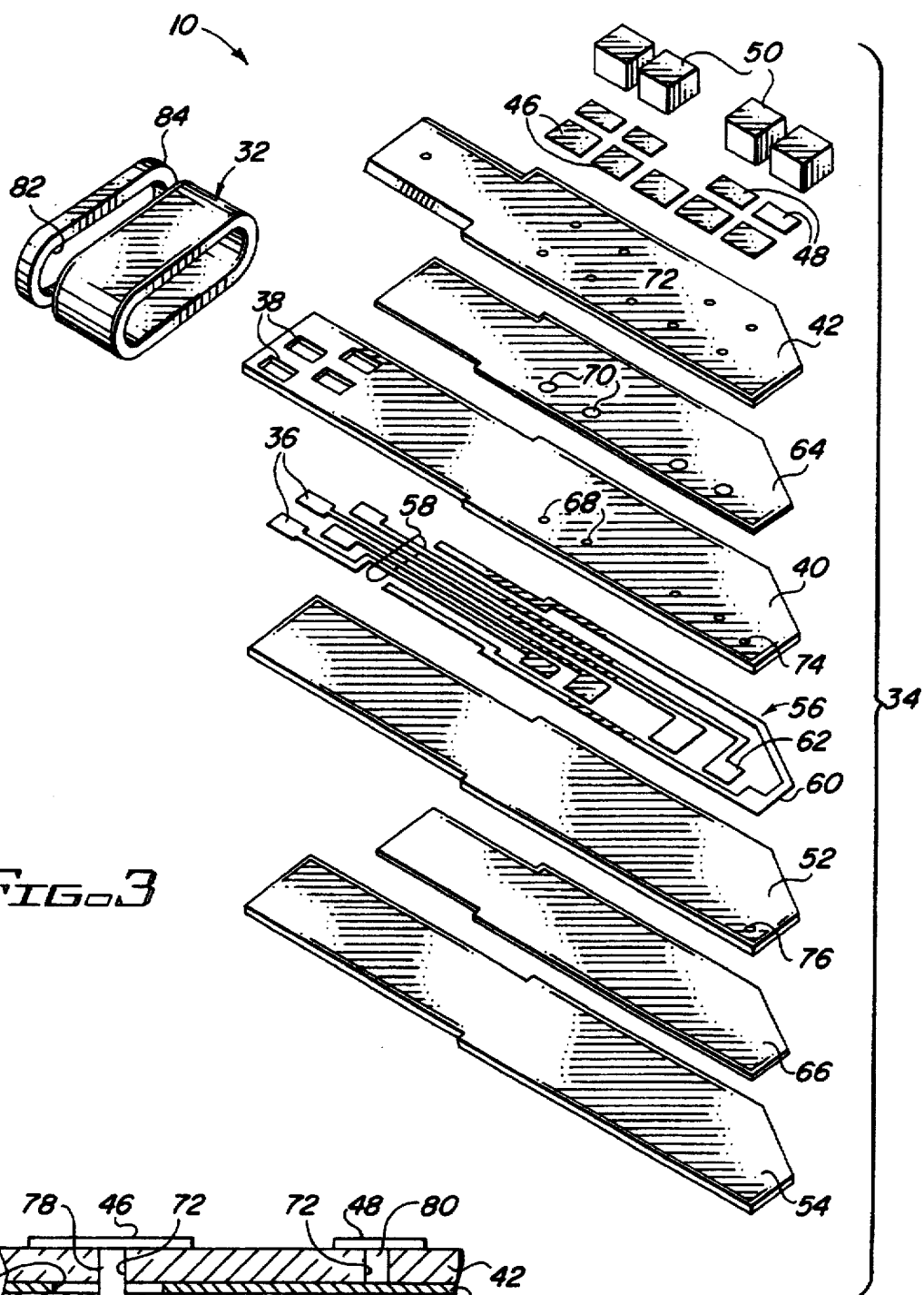
FIG. 3 is an exploded perspective view of the feedthrough assembly of FIG. 1 showing the individual parts thereof in greater detail.

The details of the feedthrough assembly 10 may be better understood with reference to the exploded perspective view of FIG. 3. As shown therein, the elongated, multilayered structure 34 includes the ceramic layers 40 and 42 in addition to ceramic layers 52 and 54. Conductors are printed on the ceramic layer 52 so as to form a generally planar array of printed conductors 56, including positive traces 58 which extend between the first and second portions 26 and 28, and a ground trace 60 surrounding the positive traces 58. The positive traces 58 terminate in the connector pads 36 at the first portion 26. Opposite ends of the positive traces 58 terminate in connector pads 62 at the second portion 28.

By printing the array of printed conductors 56 on the ceramic layer 52, the array of printed conductors 56 is sandwiched between the ceramic layers 40 and 52 which respectively form first and second ceramic layers. The first ceramic layer 40 has the apertures 38 formed therein for exposing the connector pads 36 at the first portion 26.

As shown in FIG. 3, the ceramic layers 42 and 54 form third and fourth ceramic layers respectively. A first ground plane 64 is formed by printing between the first ceramic layer 40 and the third ceramic layer 42. This disposes the first ground plane 64 on the opposite side of the first ceramic layer 40 from the conductor array 56. A second ground plane 66 is printed between the second ceramic layer 52 and the fourth ceramic layer 54, so as to be disposed on the opposite side of the second ceramic layer 52 from the conductor array 56.

Figure 4:
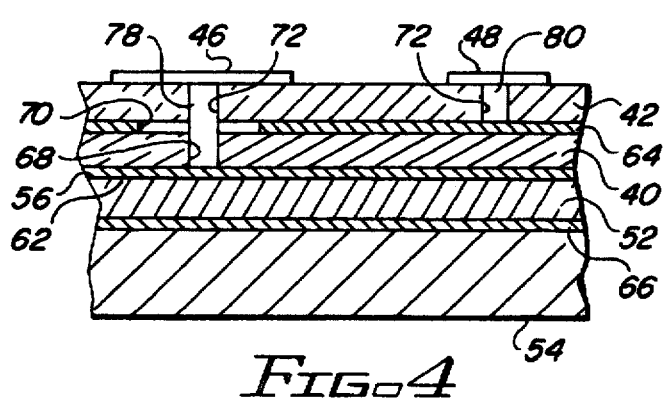
FIG. 4 is a sectional view of a portion of the feedthrough assembly of FIG. 1, showing the manner in which vias are used to couple external contacts to selected portions of the feedthrough assembly.

As described in greater detail in FIG. 4, the ground planes 64 and 66 are electrically coupled by vias to the ground trace 60 of the array of printed conductors 56 to electrically ground the planes 64 and 66. In this manner, the ground planes 64 and 66 combine with the ground trace 60, the weld ring 32 and the appropriate vias to form a conductive "boot" surrounding the signal paths of the array of printed conductors 56. By coupling the "boot" to ground, a low resistance path is presented as an alternative to the torturous path between the ground trace 60 or the ground planes 64 and 66 and the positive traces 58. Because electrical energy tends to take the path of least resistance, noise which reaches the ground planes 64 and 66 or the ground trace 60 follows the lower resistance path to ground, where it is dissipated. In this manner, electrical field shielding is provided.

As seen in FIG. 3, the first and second ceramic layers comprised of the layers 40 and 52 are disposed on opposite sides of and insulate the array of printed conductors 56, except for vias which extend through the ceramic layers 40 and 52. The ceramic layer 40 has a plurality of apertures 68 therein through which vias extend to couple the connector pads 62. Such vias extend through the apertures 68, through apertures 70 in the first ground plane 64, and through apertures 72 in the third ceramic layer 42, to the positive contacts 46 mounted on the outside of the third ceramic layer 42. The ground contacts 48 on the outside of the third ceramic layer 42 are coupled to the first ground plane 64 by vias extending through selected ones of the apertures 72 in the third ceramic layer 42. At the same time, the third ceramic layer 42 is disposed against and insulates the first ground plane 64 from the positive contacts 46 and the ground contacts 48.

The first ground plane 64 is grounded by a via which couples the ground plane 64 through an aperture 74 in the first ceramic layer 40 to the ground trace 60. The second ground plane 66 is grounded by a via which couples the ground plane 66 through an aperture 76 in the second ceramic layer 52 to the ground trace 60. The fourth ceramic layer 54 is disposed on the opposite side of the second ground plane 66 from the second ceramic layer 52 so as to insulate the second ground plane 66 from the exterior of the feedthrough assembly 10.

The filtering capacitors 50 extend between and are coupled to opposite pairs of the positive contacts 46 and the ground contacts 48. At the same time, the positive contacts 46 are coupled to the electronic circuits 12 of the cardiac pacemaker 14. The filtering capacitors 50 perform a desired filtering function by presenting a low resistance path to ground for undesirable frequencies. Because electrical energy tends to take the path of least resistance, undesirable frequencies follow the lower resistance path to ground, where they are dissipated, thus limiting the spectrum of frequencies received by the electrical circuits 12.

The sectional view of FIG. 4 illustrates the manner in which vias are used to electrically couple the various components shown in FIG. 3. FIG. 4 shows one of the positive contacts 46 and one of the ground contacts 48 at the top of the third ceramic layer 42. The positive contact 46 is coupled to a connector pad 62 in the array of printed conductors 56 by a via 78. The via 78 extends through an aperture 72 in the third ceramic layer 42, through an aperture 70 in the first ground plane 64 and through an aperture 68 in the first ceramic layer 40, to the connector pad 62. The ground contact 48 is grounded by a via 80 which extends through an aperture 72 in the third ceramic layer 42 to the first ground plane 64. In similar fashion, the first and second ground planes 64 and 66 are grounded by vias coupled to the ground trace 60 within the array of printed conductors 56. The vias, such as the vias 78 and 80 of FIG. 4, can be provided by any appropriate conventional circuit board interconnection, such as by punching or drilling, followed by conductive ink printing.

As previously described, the ceramic layers 42, 40, 52 and 54 are made of electrically insulating material. In the present example, such layers are made of alumina, although other insulating materials can be used where desired. Conductive portions of the feedthrough assembly 10 can be made of any appropriate conductive material which is printable and compatible with the electrically insulating layer material. These include the array of printed conductors 56, with its positive traces 58, its ground trace 60, and the connector pads 36 and 62, the first and second ground planes 64 and 66, the positive contacts 46 and the ground contacts 48. In the present example, such conductive members are made of platinum alloy. The weld ring 32 is made of titanium alloy, and is hermetically sealed by brazing the interior thereof with any appropriate material, such as gold alloy, to the multilayered structure 34.

The hermetically sealed housing 15 is, advantageously, made of two half clam shells (not shown) as is known in the art. When the clam shells are mated together, an aperture is formed dimensioned to fit within groove 82. The feedthrough assembly 10 is attached to the housing wall 20 of the cardiac pacemaker 14 by laser welding around a flange 84 in the direction of the arrow 86 in the exterior of the weld ring 32.

Figure 5:
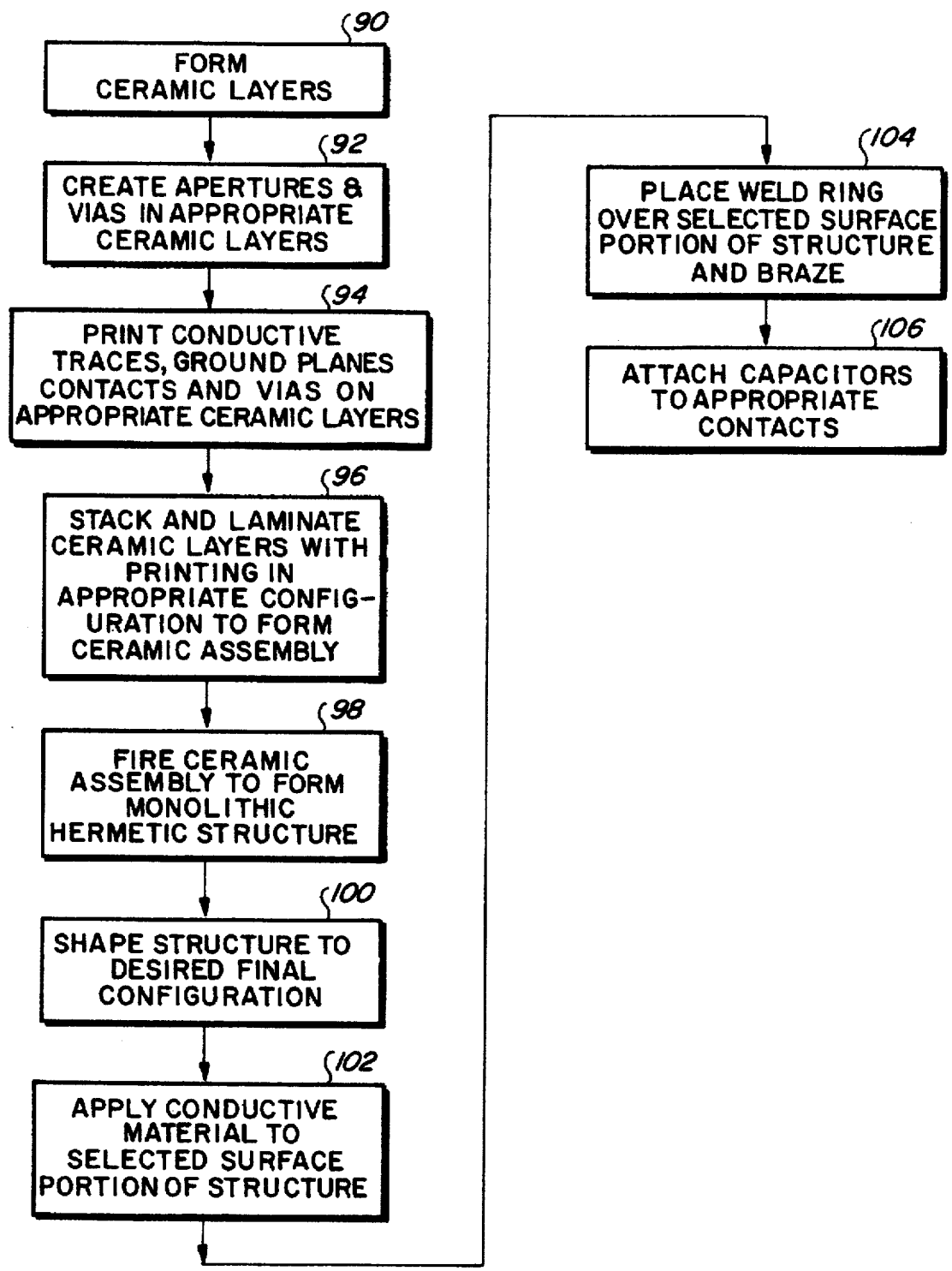
FIG. 5 is a block diagram of the successive steps in a preferred of making the feedthrough assembly of FIG. 1.

FIG. 5 shows the successive steps in a preferred method of making a feedthrough assembly, such as the feedthrough assembly 10, in accordance with the invention. In a first step 90, the ceramic layers are formed. This includes the first ceramic layer 40, the second ceramic layer 52, the third ceramic layer 42 and the fourth ceramic layer 54. In a second step 92, apertures and vias are created in the appropriate ceramic layers. Thus, the apertures 72 and associated vias are created in the third ceramic layer 42, the apertures 68 and 74 and the associated vias are created in the first ceramic layer 40, and the aperture 76 and associated via are created in the second ceramic layer 52. In a third step 94, conductive traces, ground planes, contacts and vias are printed on the appropriate ceramic layers. This includes printing of the positive contacts 46 and the ground contacts 48 on the upper surface of the third ceramic layer 42, the first ground plane 64 on the upper surface of the first ceramic layer 40, the array of printed conductors 56 on the upper surface of the second ceramic layer 52, and the second ground plane 66 on the upper surface of the fourth ceramic layer 54. Conventional screen printing techniques are used to accomplish such conductive material deposition.

In a fourth step 96, shown in FIG. 5, the ceramic layers are stacked and laminated with printing in an appropriate configuration, to form a ceramic assembly. Thus, the ceramic layers 42, 40, 52 and 54 are stacked and laminated, to form a ceramic assembly. In a fifth step 98, the ceramic assembly is fired into a final state, to form the monolithic hermetic structure. The structure is then shaped to a desired final configuration, in a sixth step 100.

In a seventh step 102, shown in FIG. 5, conductive material is applied to a selected surface portion in the region of the intermediate portion 30 of the monolithic hermetic structure. This is in preparation for welding, which takes place in an eighth step 104. In the step 104, the weld ring 32 is placed over the selected surface portion and is brazed using gold alloy to hermetically seal the weld ring 32 to the outside of the monolithic hermetic structure. In a final ninth step 106, the filtering capacitors 50 are attached to the positive contacts 46 and the ground contacts 48, to complete the feedthrough assembly 10.

While the invention has been described in connection with a preferred embodiment, it will be understood that it is not intended to limit the invention thereto, but that it is intended to cover all modifications and alternative constructions falling within the spirit and scope of the invention as expressed in the appended claims.

What is claimed is:

1. A method of electrical connection to electronic circuits inside a hermetically sealed housing of an implantable medical device to connector blocks of a connector assembly disposed outside of the hermetically sealed housing, the method comprising the steps of:

forming a hollow weld ring dimensioned to be received in an aperture of a wall of the hermetically sealed housing;

forming a multilayered structure of insulating layers with printed conductors therebetween, the printed conductors extending between a first portion and an opposite second of the multilayered structure portion and terminating in a first plurality of connector pads at the first portion for connection to the connector block and in a second plurality of connector pads at the second portion for connection to the electronic circuits;

disposing the hollow weld ring over the multilayered structure so as to have the first portion residing within the connector assembly and the second portion residing within the hermetically sealed housing;

brazing the hollow weld ring onto a portion of an outer surface of the multilayered structure;

forming a housing with an aperture dimensioned to fit about the weld ring; and welding the hollow weld ring to the housing so that the electronic circuits are hermetically sealed within the housing.

2. The method, as defined in claim 1, wherein the multilayered structure comprises a plurality of ceramic layers and wherein the step of forming a multilayered structure comprises the steps of:

positioning first and second ones of the plurality of ceramic layers so that a conductive trace is disposed therebetween;

positioning third and fourth ones of the plurality of ceramic layers so that first and second ground planes are disposed between the third and fourth ones of the plurality of ceramic layers and the first and second ones of the plurality of ceramic layers respectively, and with contacts disposed on the third one of the ceramic layers opposite the first ground plane; and electrically coupling the contacts, the first and second ground planes and the conductive trace with vias.

3. The method, as defined in claim 2, wherein the contacts include positive contacts and ground contacts, and comprising the further step of:

coupling a plurality of capacitors between the positive contacts and the ground contacts.

* * * * *